(12) United States Patent
Dignam et al.

(10) Patent No.: US 9,283,660 B1
(45) Date of Patent: Mar. 15, 2016

(54) AUTOMATED ALIGNMENT JIG FOR STANDARDIZATION OF PROSTHETIC AND ORTHOTIC DEVICES

(71) Applicants: John J. Dignam, Methuen, MA (US); Patrick P. McDermott, Vienna, VA (US); Christopher S. Anderson, Epson, NH (US)

(72) Inventors: John J. Dignam, Methuen, MA (US); Patrick P. McDermott, Vienna, VA (US); Christopher S. Anderson, Epson, NH (US)

(73) Assignee: Mentis Sciences, Inc, Manchester, NH (US)

( * ) Notice: Subject to any disclaimer, the term of this patent is extended or adjusted under 35 U.S.C. 154(b) by 321 days.

(21) Appl. No.: 13/871,738

(22) Filed: Apr. 26, 2013

Related U.S. Application Data

(60) Provisional application No. 61/639,192, filed on Apr. 27, 2012.

(51) Int. Cl.
*B25B 11/02* (2006.01)
*B23Q 1/25* (2006.01)
*B25B 1/24* (2006.01)
*B25B 5/14* (2006.01)
*B23Q 1/03* (2006.01)
*B23Q 3/10* (2006.01)

(52) U.S. Cl.
CPC . *B25B 11/02* (2013.01); *B23Q 1/25* (2013.01); *B23Q 1/03* (2013.01); *B23Q 3/102* (2013.01); *B25B 1/2463* (2013.01); *B25B 5/147* (2013.01)

(58) Field of Classification Search
CPC ...... B25B 11/02; B25B 1/2463; B25B 5/147; B23Q 1/03; B23Q 1/25; B23Q 3/102
See application file for complete search history.

*Primary Examiner* — Moshe Wilensky

(57) ABSTRACT

The present invention relates to standardizing the manufacture above-the-knee (AK) and below-the-knee (BK) prosthetic sockets and attached hardware using specially designs alignment jigs that can record position of components, with micro-encoders embedded in the jig, to quantify various degrees of freedom (rotations and translations) during integration of a temporary check socket or prosthesis. These records, together with a digital record of the shape of the truncated limb, in the form of a CAD file, can provide a complete digital record or "prescription" of the prosthesis. The digital record is then transferable to a central fabrication facility which uses a jig augmented with motors, drives systems, and encoders to robotically position and align fixtures and clamps to streamline integration and production of the prosthesis in a standardized manner.

10 Claims, 13 Drawing Sheets

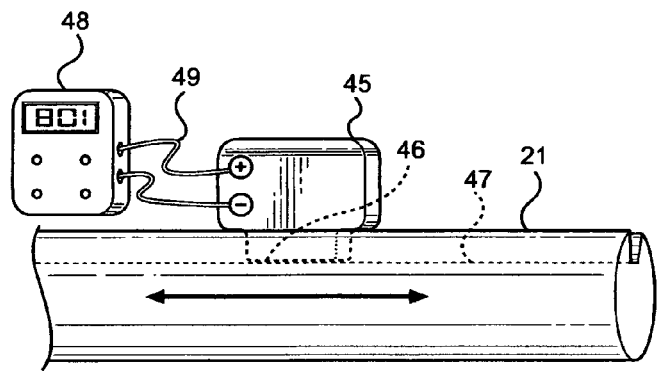
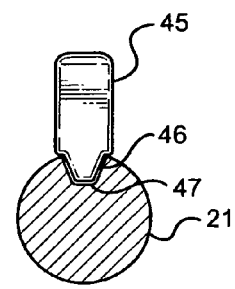
FIG. 4(a)  FIG. 4(b)
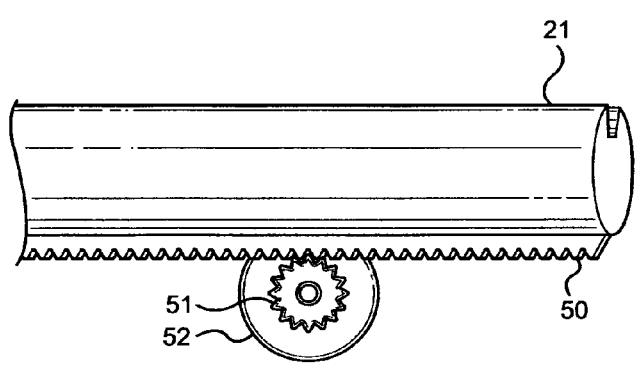
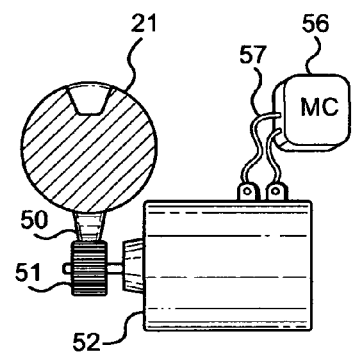
FIG. 4(c)  FIG. 4(d)

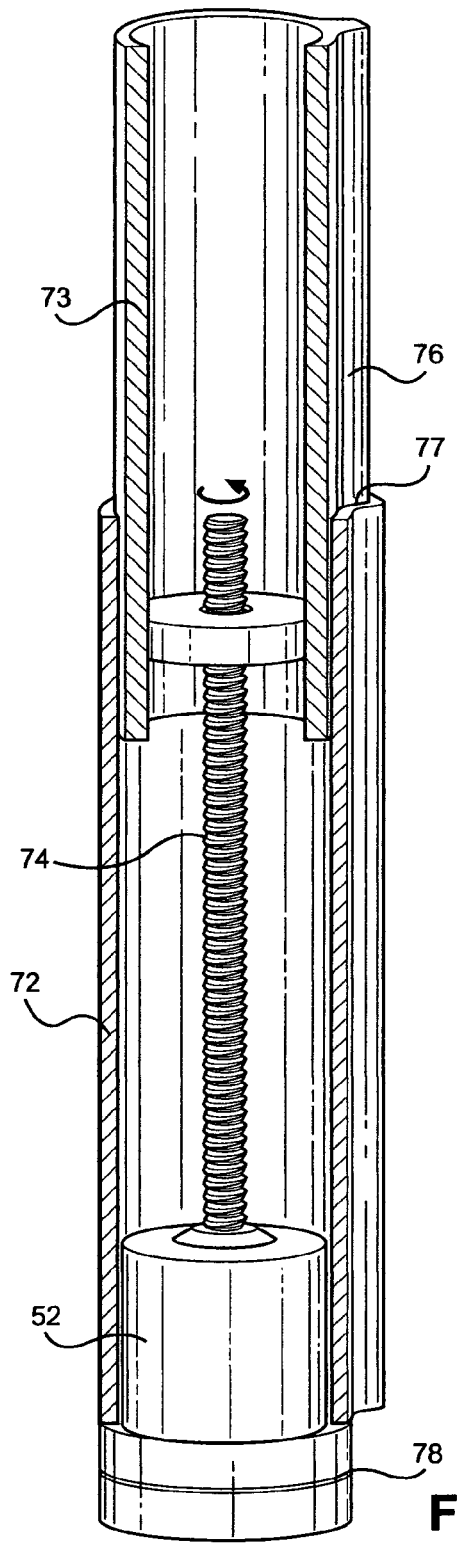
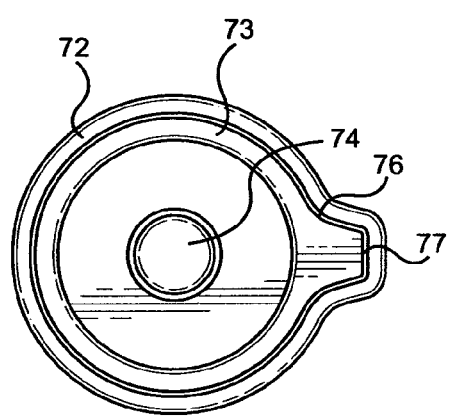
FIG. 6(e)
FIG. 6(d)

AUTOMATED ALIGNMENT JIG FOR STANDARDIZATION OF PROSTHETIC AND ORTHOTIC DEVICES

This application claims the benefits of U.S. Provisional Application No. 61/639,192, filed Apr. 27, 2012, which is hereby incorporated by reference in its entirety as if fully set forth herein.

BACKGROUND OF THE INVENTION

1. Field of the Invention

The present invention relates to standardizing the manufacture above-the-knee (AK) and below-the-knee (BK) prosthetic sockets and attached hardware. Specifically, the invention is related to the automation of the alignment jig used in the production of prosthetic devices, which incorporates sensors able translate jig settings into digital records that can be stored and, subsequently transferred to central fabrication facilities for the streamlined and low cost production of the prosthetic devices from the digital records.

2. Description of Prior Art

U.S. Pat. No. 5,926,883, issued to Ulrick A. Veith and Will W. Veith on Jul. 27, 1999, present FABRICATING ASSEMBLY AND CASTING APPARATUS FOR PROSTHETIC AND ORTHOTIC DEVICES, wherein a fabrication assembly for the manufacture of prosthetic and orthotic devices allows various components to be aligned on a common vertical mast with respect to height, distance and rotation alignment criteria.

Various parts and components for vertical jigs, some displayed in this patent application, can be found in Hosmer Tools and Fabrication Supplies Vertical Fabricating Instrument; Hosmer Tools and Fabrication Supplies Component Parts; Hosmer Tools and Fabrication Supplies Fabrication Fixtures; Hosmer Tools and Fabrication Supplies Brim Adaptor and Adjustable Brims; Hosmer Tools and Fabrication Supplies Vertical B & B Universal Casting Fixture. Similar equipment can be found in Fillauer Manuals and Brochures, and literature from other jig manufacturers and vendors. None of these, however, contain the features that will become apparent in this patent application. The innovation relates to the modification and augmentation of existing jig concepts, tools and components, with the creation of a new jig concept which contains internal sensors and actuating devices that significantly enhance the productivity of the jig.

Conventional production of above-the-knee (AK) and below-the-knee (BK) prosthetic sockets and attached hardware entails mounting various components on an apparatus like the Hosmer VFJ-100 Vertical Fabricating Jig, to provide proper alignment of the various parts that make up a prosthetic device. A prosthetic device may include the socket which fits the amputee's truncated limb, the attachment plate rigidly fixed to the socket, a pylon which connects the socket's attachment plate to an articulating or fixed ankle and/or the artificial foot. The pylon is essentially a linear structure, often a cylindrical pipe, with associate hardware for connecting the socket to the ankle or foot.

An important aspect of properly fitting the prosthetic device to the patient is the appropriate placement of the socket attachment plate to the socket, the orientation of the pylon to the attachment plate, and finally the orientation of the pylon to the ankle or foot. The alignment jig plays an important role in physically securing all of the parts, with proper orientation, during the manufacturing process.

During this process, the prosthetist, the professional clinician who fits the prosthetic device to the patient, or a technician under his or her direction, is able to secure and adjust the orientation of the component parts relative to each other on the jig. The jig has various fixtures such as clamps that can secure the parts, with flexible joints that can extend, contract and rotate the component parts to align them according to the prosthetist's judgment of best fit. As will be seen in the following descriptions, there are many degrees of freedom for setting the orientation of the parts relative to each other.

Once the alignment for best fit is achieved, the various clamps can be "locked down," meaning the clamps and joints can be secured in a fixed position, allowing the technician to remove the component parts from the jig for further processing. The jig, however, retains the settings of "best fit" until the component parts are returned to the jig for final processing and alignment. This is an advantage in that the settings are retained, but also a disadvantage in that the jig is not able to be used by others until the prosthesis is returned to the jig for final adjustments.

Currently, production of trans-tibial and trans-femoral prosthetic sockets starts with the creation of a cast of the patient's residual limb using plaster of Paris wraps or bandages to map the shape of the residual limb. After the wrap has hardened, it is carefully removed and is used as a mold for the casting of a positive plaster mold, a replica of the residual limb, with a pipe embedded in the mold in the axial direction to facilitate handling. After the mold has set, the plaster wrap or bandage is removed.

Alternatively, instead of casting a positive plaster replica of the limb in the hardened plaster wrap or bandage taken from the patient, some fabrication facilities create a digitized solid model computer file by scanning the inside of the patient's plaster wrap with a mechanical sensor or laser scanner. This digitized image can then be modified by computer software designed for this purpose to dimensionally add or subtract "material" from the digitized image in a manner similar to that of a prosthetist adding or shaving material off the plaster cast to adjust or fine tune the cast to better replicate the truncated limb.

Once the Computer Aided Design (CAD) file is generated, it can then be loaded into computer controlled CNC machine tool often referred to as a "carver", which cuts out a replica of the residual limb in a rigid but malleable material like a high density polymeric foam or wax. At this point, like the process described above for a plaster cast, a thermoforming material is drawn over the positive mold making a negative replica of the limb. This thermoform or thermoset material can be used as a preliminary "check socket" to assess how the well the socket fits the patient.

Prior to the formation of the complete prosthesis, whether from a plaster or high density foam mold, an attachment or adaptor plate is adhered to the bottom or distal end of the thermoset covered mold using an adhesive or harden able putty such as Bondo to secure the plate to the mold, and fill in voids around the plate and the thermoset covered mold. This plate is used to secure the pylon which is essentially a pipe that secures the prosthetic foot to the socket that is fitted to the residual limb. The mold is then used a mandrel for the physical layup of graphite or other high strength cloth, which is then impregnated with resin to form a rigid socket.

Most state-of-art facilities use the above methods for "digitizing" or obtaining a digital record of the shape of the truncated limb in a the form of a CAD file. What is missing, however, in order to fully characterize the prosthesis, are the parameters below the distal end of the socket related to the location and the orientation of the attachment plate on the socket, the orientation of the pylon relative to the attachment plate, and at the junction of the pylon and the ankle, the orientation of the pylon to the ankle.

In the junction of the attachment plate and the upper end of the pylon, there are adaptors that can change the angles or orientation of the pylon relative to the socket by mean of set screws that can be manipulated by the prosthetist to obtain a "best fit." Also at the distal end of the pylon there are adaptors that can change the angle or orientation of the pylon relative to the plane of the ankle attachment.

This adjustable link, the so called pyramid adapter, was patented by Otto Bock in 1969 and is used worldwide. The adapter consists of two pairs of set screws surrounding a pyramid, allowing adjustment, within a limited swing angle, in two planes. Double, eccentric and sliding adapters offer even more options. Tube adapters and tube clamps add the option of varying lengths and diameters and create an easy-to-adjust connection. The various lamination anchors, socket adapters and socket attachment blocks and provide the transition to the distal component unit. The pyramid adapters are relatively limited in the range of angles they are able to secure.

All of these settings, beyond the CAD file of the truncated limb, become key parameters in determining the final configuration of the prosthesis from socket to ankle. The object of this invention is to use an alignment jig, instrumented with linear and angular micro-encoders, to produce a fully digitized representation of the complete prosthesis, which can be used as a "prescription", much like that of an eye glass prescription, to allow a Central Fab to produce the full prosthesis using only the digital record.

The conventional vertical alignment jig like the Hosmer VFJ-100 is composed of the following parts;

1. Vertical Column Assembly—
   This is a stout cylindrical pipe with a plate or pipe grip at the bottom which allows it to be bolted or otherwise secured to the surface of a workbench. The vertical column can be aligned with a plumb bob attachment that allows the technician to precisely orient the column in the vertical or "z" direction. This vertical column can support clamp assemblies that contain horizontal shafts with fixtures at the end of each shaft that hold and align components of the prosthesis being integrated on the jig. At the back of the vertical column is a slot running the full length of the column into which a slot key on each clamp can be inserted to align the clamp on the column in a fixed position. All of the clamp assemblies can be raised and lowered on the vertical column, with a rotatable knob on each clamp that that can be tightened to "lock down" and secure the clamp to the column. A slide able collar can be positioned under the clamp assembly and tightened to allow the knob on the clamp assembly to be loosened so the assembly can be rotated in the horizontal plane and maintain a constant level in the "Z" or vertical direction.
2. Horizontal Shaft Assemblies—
   Each of the clamps cited above can accommodate and orthogonal horizontal shaft which can be extended, contracted, and rotated in the clamp fixture, with the whole assembly able to be rotated about the vertical column in the horizontal or "X-Y" plane. There are two knobs on each clamp. One locks down the shaft to the clamp assembly, and the second, the clamp assembly to the vertical column. Like the vertical column, each shaft on its top side has slots running the length of the shaft where slot keys can be inserted secure the shaft in a fixed position if so desired.
3. Upper Clamp Assembly—
   This is a fixture referred to in the Hosmer literature as the Mandrel Holding Assembly. This Upper Clamp Assembly has a fitting at the end of the shaft that allows a plaster cast to be held vertically by mans of a pipe embedded in a plaster mold (areplica, or mandrel, of the patient's truncated limb) held in place by a fixture at the end of the shaft known as a Mandrel Bushing.
4. Middle Clamp Assembly—
   This is a fixture referred to in the Hosmer literature as the Knee Holding Assembly. This assembly can have yoke-shaped fixture at the end of the horizontal shaft which allows the technician to clamp and hold larger objects like a check socket which is a thermoplastic replicas of the truncated limb. This yoke apparatus has four bolts in the semicircular yoke frame that can be tightened down to secure the object in the yoke.
5. Lower Clamp Assembly—
   This is a fixture referred to in the Hosmer literature as the Ankle Holding Assembly. The horizontal shaft has a fixture on its end with a horizontal plate that can be moved side to side in the X-Y plane by a screw mechanism. This plate can hold the attachment mechanism for pylon to the ankle or foot.

As one can see, there are numerous degrees of freedom built in to the convention alignment jig, with clamp assemblies able to be raised and lowered on the vertical column in the "Z" direction, and rotated about the vertical column in the "X-Y" plane. Furthermore, horizontal shafts with fixtures on the ends can be, extended, contracted, and rotated within each clamp assembly. The fixtures themselves can have internal degrees of freedom, such as the positioning of objects in the yoke in the Middle Clamp Assembly, and the positioning of the pylon-ankle attachment in the Lower Clamp Assembly.

Beyond the extensions and rotations described above, there are other minor angular adjustments that can be made at specific sites using what are known as single and dual pyramid adaptors. In these adaptors, the relative angles of male and female adaptor plates, within a few degrees of rotation, can be adjusted with four screws in the female component tightened against sloping sides of the male pyramid component. These pyramid adaptors can be found at the socket and ankle ends of the pylon as well as at the end of the Upper Clamp Assembly shaft when coupled with a rotatable joint affixed to the Mandrel Bushing.

Once the technician has assembled the various components on the jig, aligned them, and locked down all of the setting, the jig itself stores the settings while the technician continues on to the production of the prosthesis. The jig now unable to be used for other production until the technician has finished the original prosthesis. Furthermore, once the jig is used for production of a different prosthesis, the original settings are essentially lost. If another duplicate socket is required at a later date, the process must be repeated from scratch, requiring new settings to be generated.

This invention relates to the recording and reproduction of major settings related to the alignment of the prosthesis, allowing the prosthetist flexibility to make minor adjustments by means of the single and dual pyramid adaptors described above.

SUMMARY OF THE INVENTION

This invention envisions a complete system for standardizing the prosthesis manufacturing process by: 1) digitally recording and storing the complete digital record of the prosthesis including the truncated limb CAD file and the orientation of the pylon with attachments relative to socket and ankle, generated at the Patient Care Facility: 2) transmission the complete digital image and pylon orientation to the Central Fabrication Facility, the Central Fab; 3) production of the complete prosthesis at the Central Fab which is then returned to the Patient Care Facility for final fitting; 4) the storing of the complete prosthesis digital record in central secure data base for future use in replication of an existing prosthesis or a starting point for a modification of the record as the truncated limb The key to this standardization process is modifying or creating new forms of the alignment jig now used in the industry to produce a complete digital record of the prosthesis at the site where the prosthetist is fitting the patient, and to allow the utilization of that record at a Central Fab to produce the aligned socket and attachments. The concept includes two potential forms of the new alignment jig:

1. The Digital Alignment Jig—
    This is an alignment jig where the principle degrees of freedom used by the prosthetist to manually align the socket to the pylon through extension and rotation of clamps and fixtures, to be instrumented with linear and rotary micro-encoders that fully characterize the linear and angular measurements "locked down" by the prosthetist after the "best fit." These parameters are simultaneously recorded on a PDA or other device which, along with the CAD file, constitute the Complete Digital Record. Once recorded, the jig could be used for other alignments, with the jig reset later, manually, with the technician resetting the clamps and fixtures manually, but with the aid of the digital readout of linear and rotational settings on the PDA.
2. The Automated Alignment Jig—
    This is a further refinement of the Digital Jig which turns the jig into a robotic device, with the addition of motors and drives, able to physically reproduce the clamp and fixture alignment settings that were locked down by the prosthetist who recorded the original digital record. This added functionality would allow a technician to reset all of the clamps and fixtures without having to manually raise, lower or rotate fixtures.

The Digital and Automated Jigs could be resident at either/or both of the above mentioned facilities, at the office of the prosthetist or at the Central Fab. The Automated Jig would, however, cost significantly more than the Digital Jig and may be affordable only as a system for the Central Fab, where numerous sockets would be in production at any time.

Beyond the benefits to the prothetist and the Central Fab, the above system could be of great value to organizations like the Veteran's Administration or Health and Human Services, which has oversight over Medicare and Medicaid reimbursements, by maintaining a central HPPAA-compliant protected data bases on the AK and BK "prescriptions" for patients under their care This allows almost instantaneous reproduction of prostheses at an efficient Central Fab contract facility, if a prosthesis is lost, broken, or requires a re-fitting. The prothetist could modify the CAD file and even the pylon orientation and store the reformatted Digital Record for future use.

In the case of the Digital Alignment Jig (DAG), the invention relates to modifications to the standard alignment jig or an alternative jig design concept which incorporates sensors that are able to automatically record all of the settings when the jig is "locked down" after a prosthetic device is assembled and aligned on the jig. This involves linear and rotational micro-encoders that record the position and rotation of the clamp assemblies on the vertical column as well as the extensions, contractions and rotations of the horizontal shafts, with the various fixtures on the upper, middle and lower clamp assemblies. The micro-encoders themselves could be analog or digital, however, their output will likely be displayed as numerical digital readouts, or digital data communicated to a PDA or other device that records, stores, or transmits the data.

Linear encoders are sensors, transducers or read heads paired with scales that encode position along a linear path. The sensor reads the scale and converts the position into an analog or digital signal which is then decoded by a digital readout specifying position along the linear path. Micro-encoder technologies exploit many different physical properties to encode position including: optical, magnetic, inductive, capacitive and eddy current.

Optical encoders utilize transmission of light through or reflection from a scale which is coded according to position on the linear path. Light sources include LEDs miniature light-bulbs or laser diodes. Magnetic encoders employ active magnetized or passive variable reluctance scales where position is sensed with sense coils, Hall Effect, or magneto-resistive read heads. Capacitive encoders sense the capacitance between the scale and the reader. Inductive micro-encoders use principles of electromagnetic induction and coils to sense position along the linear path. Eddy current uses scales coded with high and low permeability detected with a inductive coil sensor that senses changes in inductance in an AC circuit.

Although, in principle, all of these technologies would be candidates for sensing in the Digital Alignment Jig, the choice would depend on several factors, including, cost, ability to sense in a dirty environment (e.g., plaster dust), and ability to be incorporated in the jig without impairing its operation. Linear alignment position settings would include: vertical height of the various clamp assemblies from the base of the jig, horizontal positioning of the shafts in each clamp assembly which contain fixtures for securing the prosthesis parts, and certain of the fixtures, like the linear positioning of the pylon-ankle attachment in the Lower Clamp Assembly.

Rotary encoders measure angular rotation of a body relative to a fixed reference such as a shaft rotation in the clamp assembly cited above. The shaft micro-encoders that use some of the principles articulated above, to convert angular position into an analog or digital code, but mainly rely on optical or mechanical means. In an optical micro-encoder a photo detector array reads an optical pattern on a disc contained in the micro-encoder, which is then translated into position by a microprocessor or microcontroller. In a mechanical micro-encoder, contacts touch a disc composed of conductive and non-conductive patterns in concentric rings that containing binary codes related to position. These are decoded electronically to establish the angle of rotation of the shaft.

There are a number of degrees of freedom in the Digital Alignment Jig that relate to angular motion or settings, that can be determined with rotary micro-encoders. These include, as will be seen in the following discussions, rotations of horizontal shafts held in the clamp assembly, rotation of the fixtures holding the prosthetic parts when the clamp shafts are stationary (when, for example, the slot keys are engaged in the shaft slots), rotary motions of the clamp assembly in the horizontal plane, when the vertical slot keys are not engaged, and certain angular rotations related to Upper Clamp Assembly shaft when coupled with a rotatable joint affixed to the Mandrel Bushing.

The Automated Alignment Jig (AAJ) is a further refinement of the Digital Jig which turns the jig into a robotic device, with the addition of motors and drives, able to physically reproduce the clamp and fixture alignment settings that were locked down by the prosthetist who recorded the original digital record. The Automated Jig would contain the sensors described above in the Digital Jig, but would use the digital signals in a feedback loop to physically raise and lower the various clamp assemblies on the central alignment column, extend and retract shafts attached to the clamp assemblies, and rotate fixtures that hold the prosthesis parts during the process of alignment.

OBJECT OF THE INVENTION

The object of the invention is to provide for a system the streamlines and standardizes the system for production of prosthetic devices by securing a complete digital computerized record or "prescription" of the temporary prosthetic socket and attachments generated at the Patient Care Facility, for use used by a Central Fabrication facility to reproduce the final form of the prostheses accurately and economically.

It a further object of the invention, to provide the means of standardization by developing an alignment jig which can record digitally, all of the alignment jig settings that were generated by the prothetist at the Patient Care Facility when creating and aligning the temporary check socket used by the prothetist to obtain the best fit to the patient.

It is a further object of the invention to augment the alignment jig with motors and drives that are able to position the clamps and fixtures at the Central Fab and create, in effect, a reproduction of the settings generated at the Patient Care Facility, in order to expedite the rapid and affordable production of the final prosthesis, including the socket, the pylon, and attachment plate for the ankle/foot.

It is a further object of the invention that the complete data record generated by the alignment jig sensors is formatted in a standardized manner for storage in secure HIPPA-compliant facility, for future use by government and/or commercial entities for reproduction and modification of prosthesis for future patient needs.

It is a further object of the invention to provide a standard set of procedures with automated tools to lower the cost of manufacturing prosthetic devices through the reduction of labor costs and reduction of errors by automated replication of settings required to fabricate the prosthesis.

It is a further object of the invention to maintain a complete digital description or prescription of the prosthesis to avoid having to store plaster casts of the truncated limb or check sockets, or other physical representations of the truncated limb at the Patient Care Facility and/or having to ship such objects to the Central Fab for fabrication of the permanent prosthesis.

These and other objects of the present invention will become apparent upon further review of the following specifications and drawings.

BRIEF DESCRIPTION OF THE DRAWINGS

Various objects, features, and attendant advantages of the present invention will become more fully appreciated as the same becomes better understood when considered in conjunction with the accompanying drawings, wherein:

FIG. 4(a) is a perspective side view of a slotted horizontal shaft with a micro-micro-encoder transducer head contiguous to and inserted in the slot.

FIG. 4(b) is an end view of the slotted horizontal shaft with a micro-encoder transducer head contiguous to and inserted in the slot.

FIG. 4(c) is a perspective side view of a horizontal shaft with a rack and pinion drive system attached to the bottom of the shaft with gear and drive motor.

FIG. 4(d) is an end view of the slotted horizontal shaft with the rack and pinion drive system showing gear and drive motor.

FIG. 6(d) is a side view of screw drive system with the telescoping shaft extended by rotary motion of the screw.

FIG. 6(e) is a top view of the screw drive system showing a guide rail within a slot to prevent rotation of the extending member as it is being extended.

DETAILED DESCRIPTION OF THE PREFERRED EMBODIMENTS

The Figures illustrate the key elements of the baseline Automated Alignment Jig (AAJ) and its variants. One of the principal variants is the Digital Alignment Jig (DAJ) which includes the sensor elements only (linear and rotary actuators). The DAJ, however, can provide a complete digital data representation of the settings on the jig when it is "locked down," after the prosthetist has established a best fit to the patient. The AAJ is a more complex device, augmented with motors and drives that robotically establish the fixture orientations derived from the DAJ.

Figure 1:
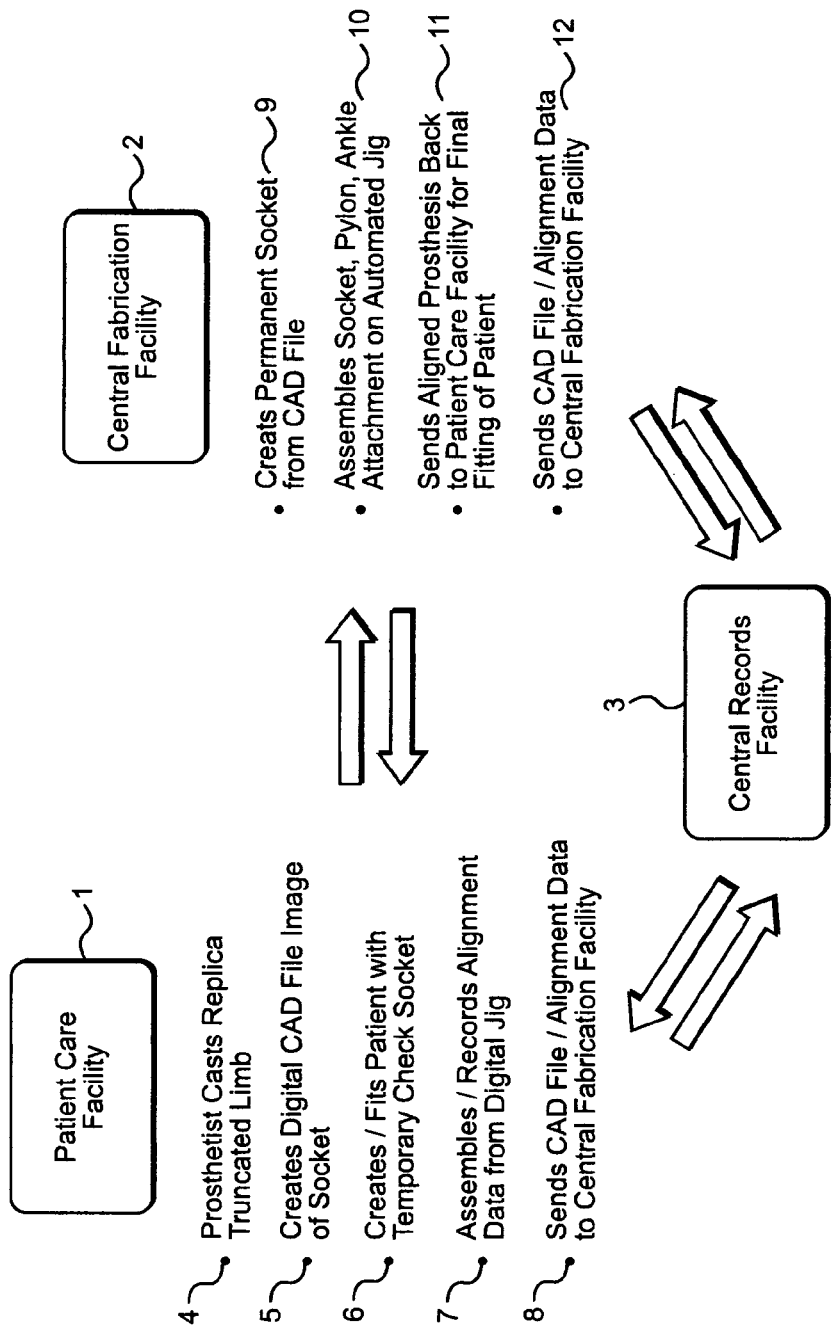
FIG. 1 is a schematic of the practices and inter-relationships of three key facilities that embody a more affordable standardized institutional approach to prosthetic device manufacture.

FIG. 1 is a schematic showing the institutional framework in which the AAJ and the DAJ function to standardize and streamline the prosthetic device production process. The Patient Care Facility 1 is a local or regional center staffed by prosthetists, trained in diagnosing, treating, and fitting patients with prosthetic devices. Some of these centers have in house capability to fabricate prostheses, requiring labs and lab technicians, which may or may not have the throughput required for full staffing. Some of these centers, which do not have in house capabilities, have to rely on Central Fabrication Facilities 2, called Central Fabs, to manufacture the prostheses.

In order to fill orders, using conventional methods, the Patient Care Facility 1 has to physically send plaster wraps, casts, or check sockets, with written instructions to the Central Fab 2 in order to specify the manufacture of a prosthesis. This process is somewhat cumbersome, time consuming, costly, and subject to error. The goal of the invention described here is aimed at setting up the Patient Care Center with the necessary equipment so that the prosthetist can fully describe the prosthesis in terms of the complete digital record which may be stored in an Central Records Facility 3, that is accessible through secure links to both the Patient Care Facility, as the Central Fab. The Central Records Facility is HIPPA Compliant (Health Insurance Portability and Accountability Act of 1996-"HIPAA") with Privacy Rule standards that address the use and disclosure of individuals' health information. The following steps are required to generate this file.

The prosthetist generates a replica of the truncated limb 4 by wrapping a plaster impregnated bandage around the limb and removing it after it hardens. At this point, the prothetist, if properly equipped, can generate a CAD (Computer Aided Design) file using a laser or touch sensors to scan the inside of the wrap 5 which represents the inside dimension of the socket. The prosthetist can then pour plaster into the plaster wrap, to generate a positive image of the limb in plaster. Using the plaster mold as a mandrel, the prothetist then draws a heated thermo set plastic over the mandrel and creates a negative image of the limb.

Alternatively, if the equipment is available, the prosthetist can also carve a positive image of the limb in high density foam, using a computer controlled machine tool, controlled by the CAD file described above. A negative image can be formed in plastic using the heated thermoset material.

However this plastic replica is formed, it can be used to create a "check socket" with the addition of a socket attachment plate, pylon, and foot, formed on an alignment jig. The prosthetist uses this temporary check socket to work with the patient and assure a proper fit 6. By using the Digital Alignment Jig (DAJ), the prosthetist is able to record all of the alignment settings digitally. This data together with the CAD file forms the complete digital record or prescription of the prosthesis 7. This prescription can then be sent electronically 8 directly to the Central Fab 3 or to the Central Records Facility 3 where it is accessible by the Central Fab.

FIG. 1 shows the interaction of the Patient Care Facility with the Central Fab, where the Central Fab now creates a permanent socket 9 in graphite epoxy or other composite material, using the complete prosthesis data file 7 sent from the Patient Care Facility. Since the data file 7 is sent electronically, the Central Fab can begin production of the Prosthesis immediately, as soon as the Patient Care Facility "locks down" the final alignment settings. In conventional practice, the Patient Care Facility would have to physically send the plaster wrap, the plaster mold, the check socket or other artifacts to the Central Fab.

Using the Automated Alignment Jig (AAJ), technicians at the Central Fab can assemble the socket, pylon, and ankle attachment on the Automated Alignment Jig 10. The Central Fab now sends the aligned prosthesis back to Patient Care Facility for final fitting of the patient. The prosthetist is able to slightly modify the angles of the various prosthesis components within a very limited range using pyramid adaptors described above.

After the prosthesis is produced at the Central Fab, the complete CAD/alignment digital file 7 is sent to the Data to Central Records Facility 13.

Figure 2:
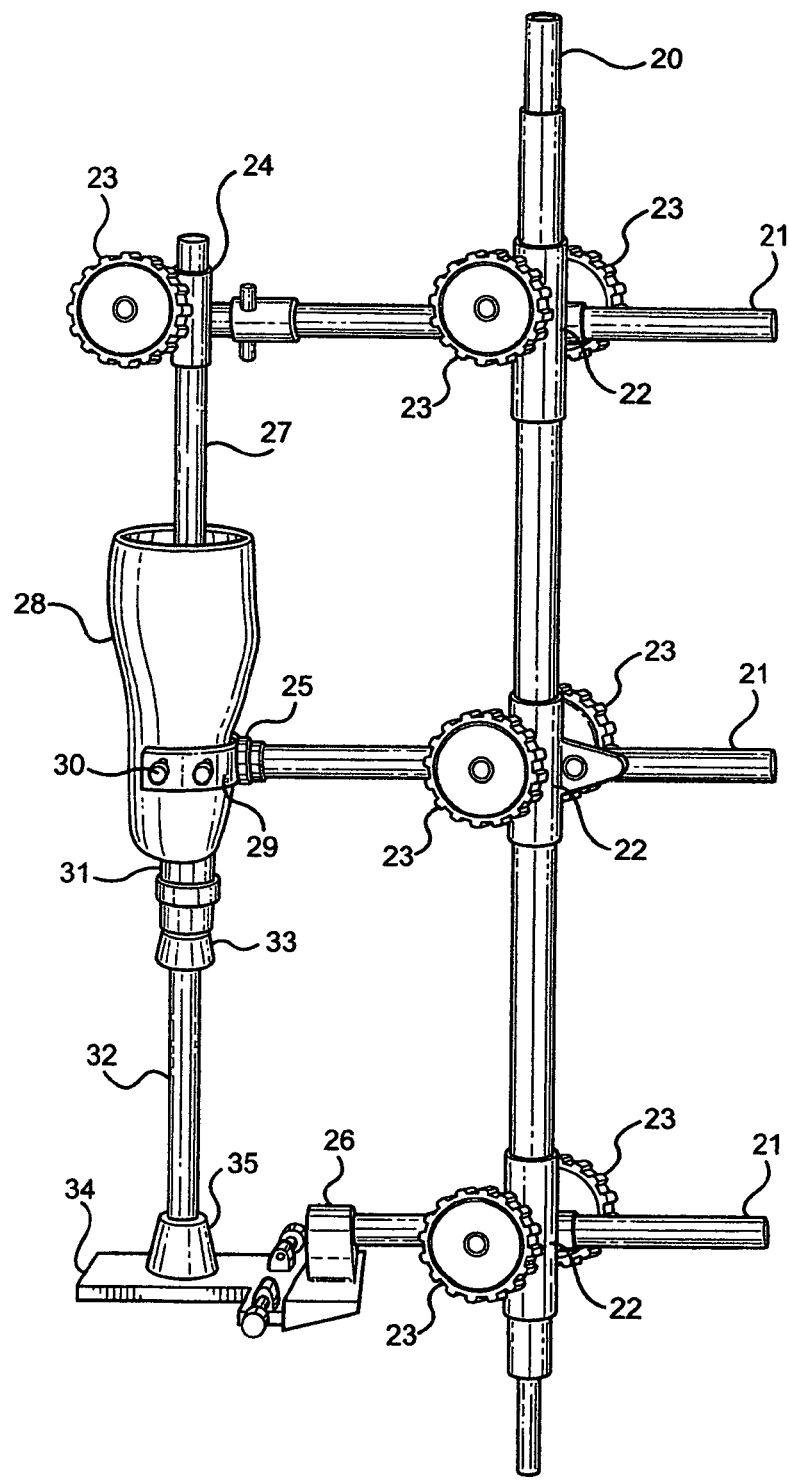
FIG. 2 is a perspective view of a conventional vertical alignment jig with clamps and fixtures securing a plaster mold, with pylon and attachment plates.

FIG. 2 shows a prosthesis being assembled on a jig. Jig structure is composed of a central vertical column 20 supporting horizontal shafts, by means of clamp fixtures 22 that allow the column and the shafts to move freely in the clamp assembly, but are able to be secured in a fixed position by the rotation of knobs 23 that tighten the clamp assembly around the vertical column 20 and the horizontal shafts 21 that are held orthogonal to the column by means of the clamp assembly structures 22. The shafts at their distal ends to the left support specialized fixtures 24, 25, and 26 that hold and support the various prosthesis components that are being aligned on the jig.

Fixture 24, the fixture attached to the shaft in the top level clamp assembly is a cylindrical fitting called the socket clamp assembly. This fixture is capable of holding a cylindrical pipe 27 embedded in a plaster mold 28. The pipe is secured by rotation of a knob 23 that tightens the fixture around the pipe. Mold 28 is supported by a yoke 29 attached to the shaft in the mid-level clamp assembly. The yoke has four screws 30 that surround and are tightened against the mold securing it to the fixture.

An attachment plate 31 is secured to the distal end of the socket with adhesive, and oriented by the prosthetist to assure that the pylon 32 is properly oriented with respect to the axis of the socket represented by pipe 27 embedded in the plaster mold 28.

The proximal end of pylon 32 can be attached by a pyramid adaptor 33 via screws into the socket attachment plate 31. Likewise, the distal end of the pylon can be secured to the base 34 of the ankle bracket assembly fixture 26 via another pyramid adaptor 35 screwed or bolted to base 34.

Figure 3A:
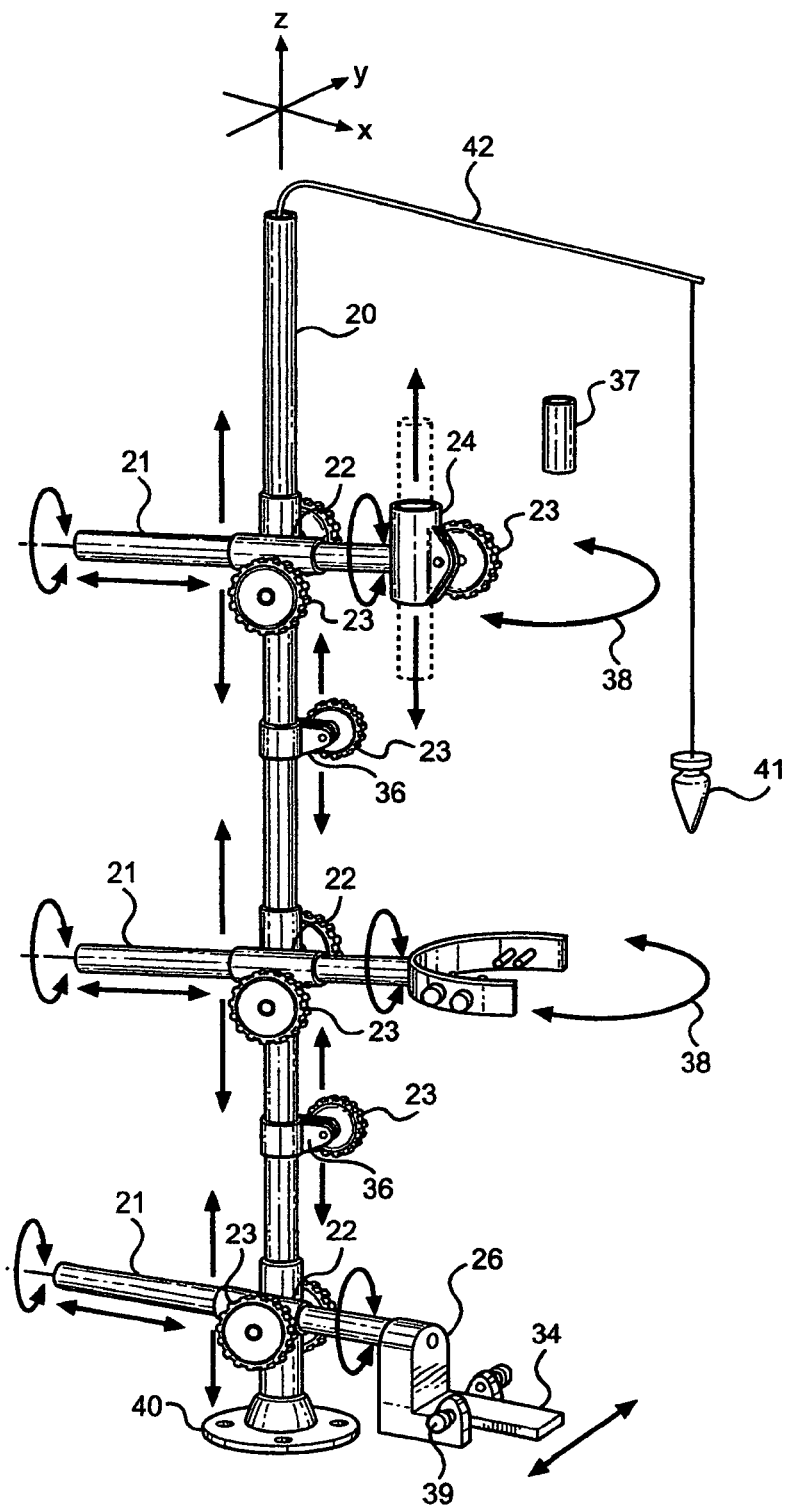
FIG. 3(a) is a perspective view of a conventional vertical alignment jig showing the various degrees of freedom able to be exercised in securing a prosthetic assembly to the jig.
Figure 3B:
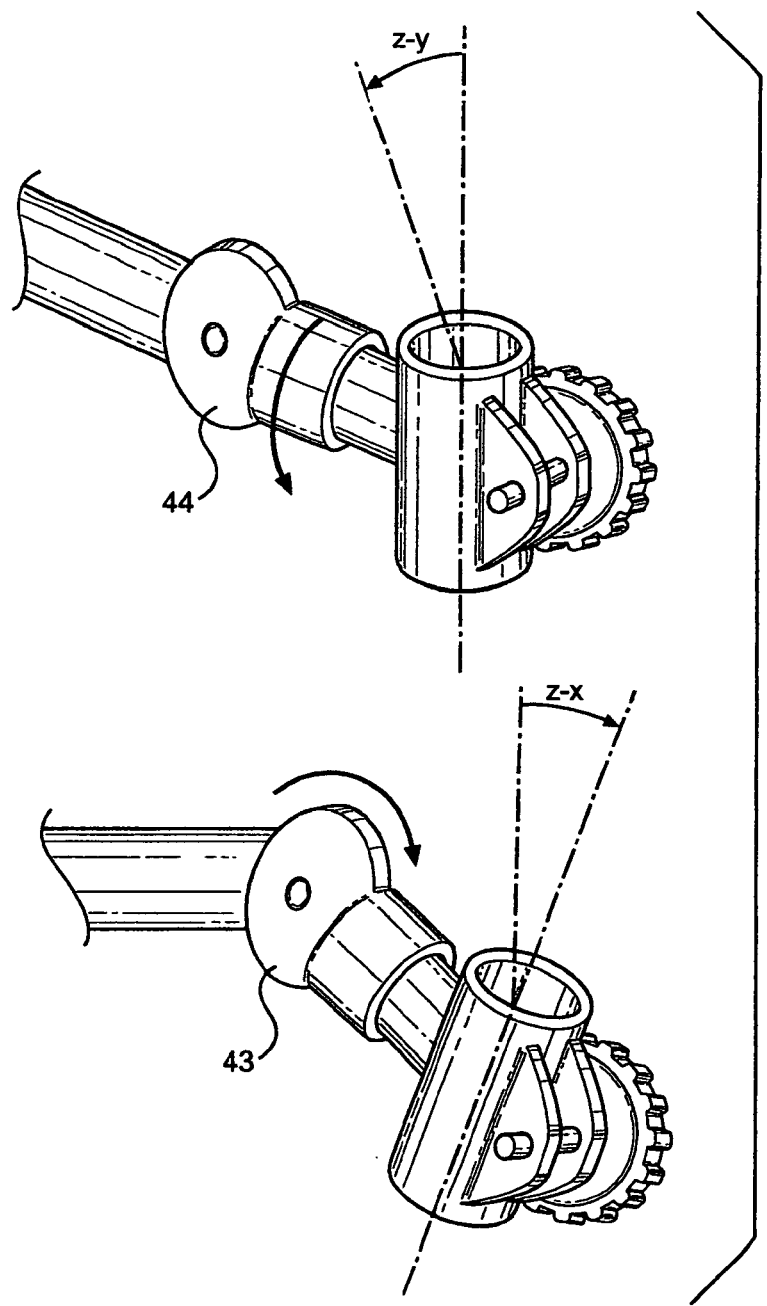
FIG. 3(b) is a perspective view of the upper horizontal shaft fixture with joints allowing rotations in the Z-X and Z-Y planes.

FIGS. 3(a) and 3(b) show allowable degrees of freedom for the various jig components that allow the prosthetist to assemble prosthesis components on the jig fixtures, and align the various components at angles and extensions required to obtain "best fit."

Clamp assemblies 22 can be raised and lowered on column 20 in the "z" direction to alter the height of horizontal shafts 21, and be secured at a fixed height by rotation of clamping mechanisms 23. Likewise, each of the horizontal shafts 21 can be extended and contracted along the "X" axis and can be rotated in a clockwise or counter-wise direction, and secured by the rotatable clamping mechanism 23.

To establish a fixed position on the vertical column, a positioning collar assembly 36 can be raised up and positioned under clamp assembly 22, and secured by tightening rotatable knob 23. With the collar in place, the clamp assembly itself 22 can be unlocked and raised up to remove, for example, prosthesis components like the plaster mold 28 which may have to be removed from the jig to continue processing. The collar retains the setting on the vertical column so the raised clamp assembly can be returned to its original position when the mold or check socket is returned to the jig.

There are also degrees of freedom associated with various fixtures described in FIG. 2. The socket clamp 24, for example, can be rotated clockwise CW and counter clockwise CCW with respect to shaft 21. The pipe embedded in the plaster mold can be raised and lowered in socket clamp 24, and secured by rotating knob 23. Pipes of different diameters can be accommodated by insertion of bushings 37 which compensate for the differences and are secured by knob 23.

With the clamp mechanism 23 of the upper clamp assembly 22 released, the whole assembly including shaft 21 and fixture 23 can be rotated in the Z-Y plane, about the vertical column 20, where it can be moved from side to side 38 if needed, to align the components.

The same types of movement are allowable for the mid-level clamp assembly 22, where the fixture, here the yoke 29, is rotatable CW as well as CCW, relative to shaft 21, and the whole assembly, including yoke, able to be rotated in the Z-Y plane 38.

The lower level clamp assembly 22 supports the ankle assembly fixture 26 at the end of shaft 21 with a moveable platform 34 positioned by a rotatable screw 39 that is able to translate the platform in the y direction, and together with the slideable shaft 21 is further able to translate the platform in both the Y and X directions within the X-Y plane, as well as rotate the platform in the Z-Y plane. The vertical column 20 can be secured by a base plate 40 to a workbench and aligned vertically by bob 41 supported by rod 42 attached to the top of the vertical column.

FIG. 3b shows additional degrees of freedom allowable in the upper socket clamp assembly fixture 24 which is able to be tilted in the Z-X plane by means of joint 43 or rotated in the Z-Y plane by means of joint 44.

Figure 4E:
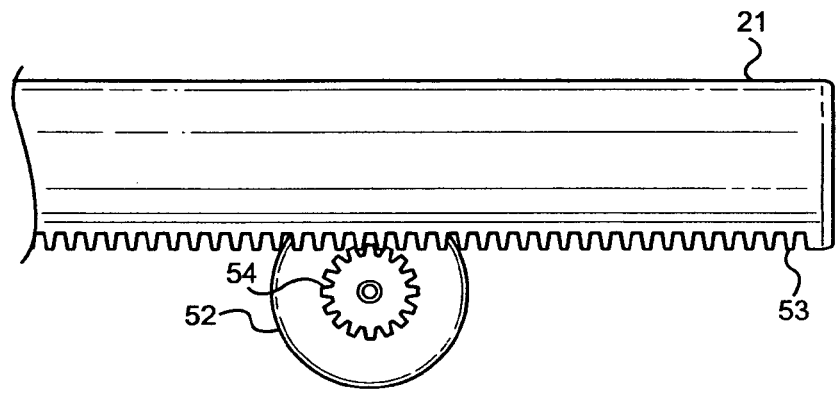
FIG. 4(e) is a side view of an alternate drive system where slots are milled directly into the bottom of the horizontal shaft to accommodate a rack and pinion drive system.
Figure 4F:
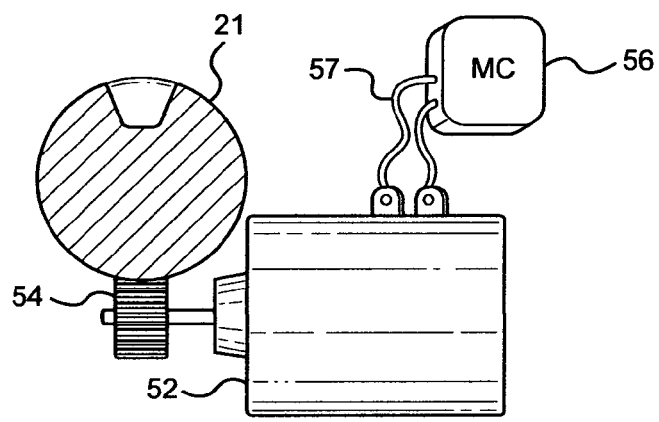
FIG. 4(f) is an end view of the alternate drive system with gear and drive motor directly engaging the slots milled in bottom of shaft.
Figure 4G:
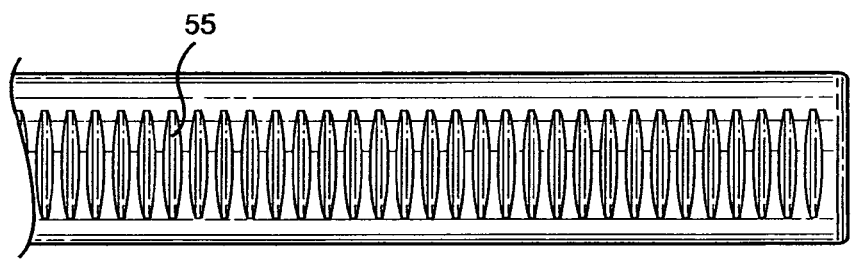
FIG. 4(g) is a bottom view of the shaft in FIG. 4(e) showing the array of slots milled into the horizontal shaft.

FIG. 4(*a*) through 4(*g*) illustrate the sensing and positioning of shaft 21 by mans of linear encoders and fractional horsepower motors geared appropriately to move the various elements through rack and pinion drive trains. FIG. 4(*a*) is a side view of slotted shaft 21 with a small linear transducer 45 with readout head 46 with appropriate materials responsive to the sensor (optical, magnetic, inductive, capacitive, etc.) embedded in the slot. FIG. 4(*b*) is an end view showing the read out head 46 in the slot. The linear encoder 45 is connected to a digital readout 48 by means of cabling 49.

FIG. 4 (*c*) is a side view of shaft 21 with a rack and pinion drive including an external structure 50 with teeth cut into it meshing with gear 51 on the electric motor 52. FIG. 4(*d*) is an end view of FIG. (c). FIG. 4 (*e*) is a side view of shaft 21 with a rack and pinion drive using teeth 55 milled directly into the bottom of the shaft, and gear 54 meshing with the teeth. The electric motors 52 are powered by a motor controller (MC) 56 via power cables 57.

FIG. 5(*a*) through 5(*e*) illustrated the sensing and rotation of various shafts or fixtures by means of rotary encoders controlling fractional horsepower motors geared appropriately to move the various elements through gearing and worm drive trains. FIG. 5(*a*) is a side view of a fixed shaft 21a connected to a rotary shaft 21b through joint 58, with angular data from rotary micro-encoder 59 recorded on digital read out 60, connect through cables 61.

FIG. 5(*b*) is a side cut away view of a geared motor-driven transmission system for rotating shaft 21b relative to stationary shaft 21a where a large planer gear 62 attached to shaft 21b is free to rotate, supported by bearing 63, and is driven by motor 52 through gear 64 which meshes with gear 62. Housing 65 provides the necessary support structure for these components.

FIG. 5(*c*) is a cut away end view showing the placement of the motor 52 with gears 62 and 64, contained within housing 65.

FIG. 5(*d*) is a cut away end view of an alternate drive system where motor 52 is orthogonal to the shafts and is linked to planar gear 62 by worm drive 66, contained within alternate housing 67.

Figure 5A:
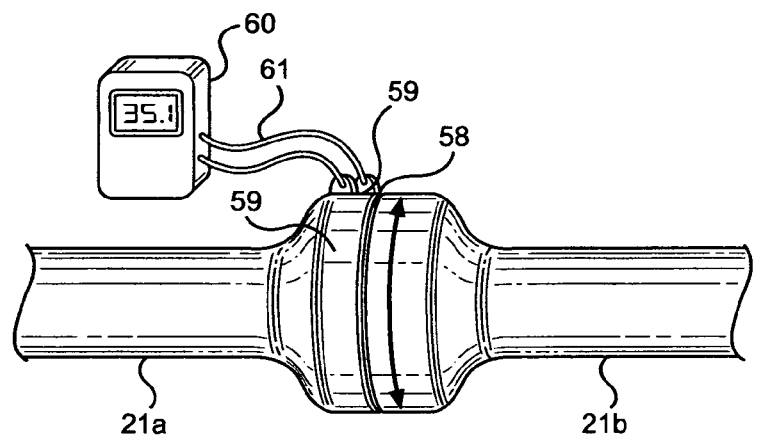
FIG. 5(a) is a perspective side view of a rotary joint with embedded rotary micro-encoder attached to a digital display.
Figure 5B:
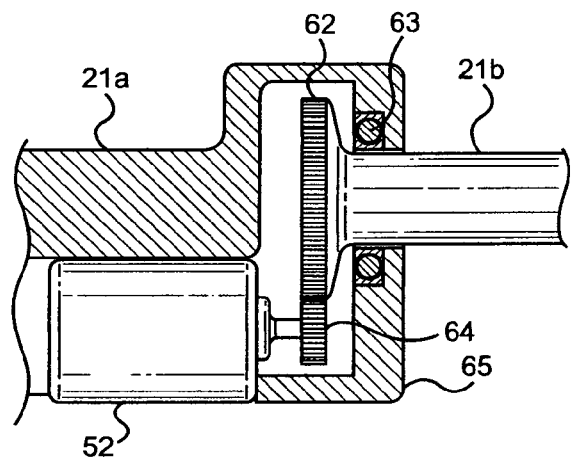
FIG. 5(b) is a side view of a rotary joint with a gear drive system and motor able to rotate the shaft on one side of the joint relative to the other.

FIG. 5(*e*) is a cut away side view with the drive mechanism of FIG. 5b integrated with the rotary encoder of FIG. 5a.

Figure 6A:
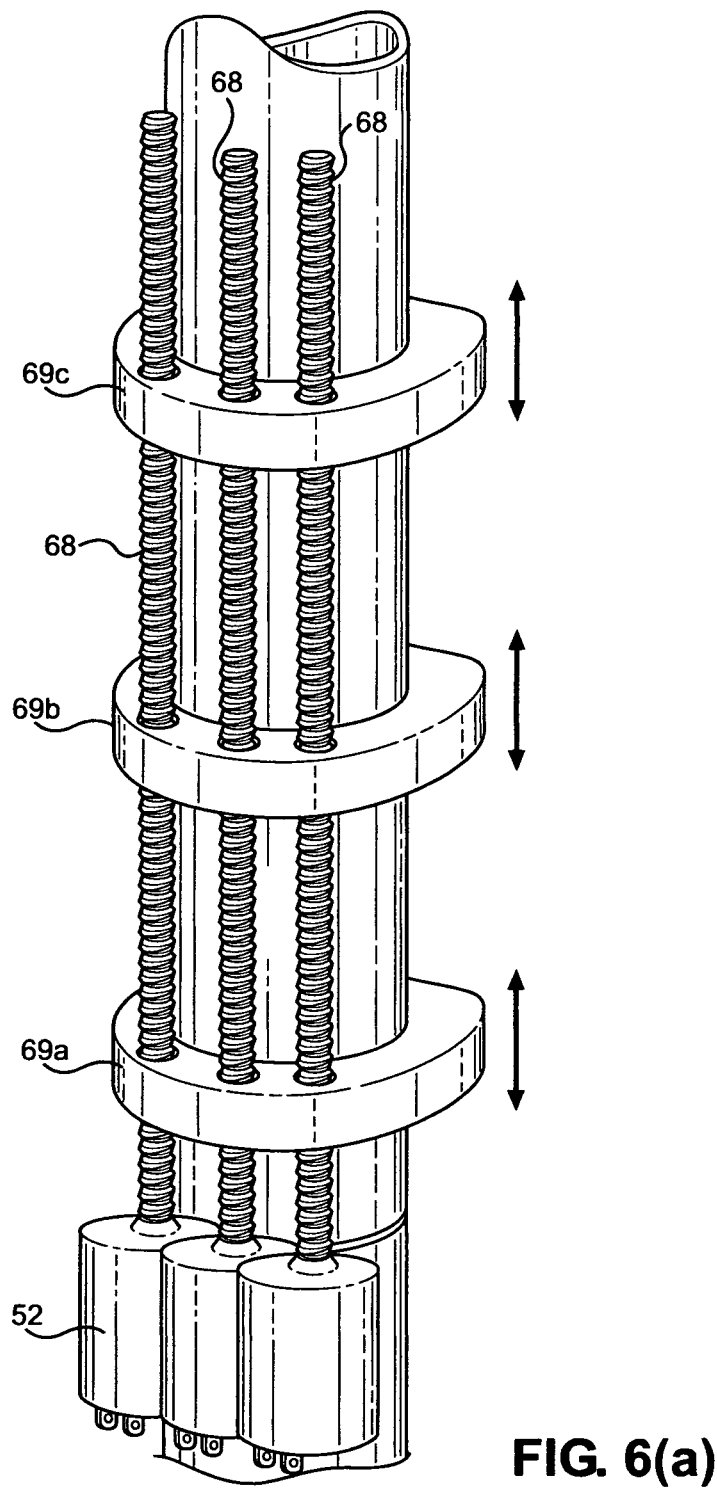
FIG. 6(a) is a perspective side view of an external motorized screw drive system with three collars to raise and lower the clamp assemblies on the jig's vertical column.
Figure 6B:
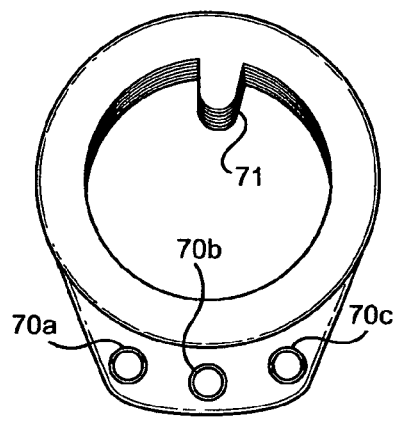
FIG. 6(b) is a top view of a collar with one threaded hole matching threads on one screw, and two larger diameter holes allowing collar to traverse other two screws unimpeded.
Figure 6C:
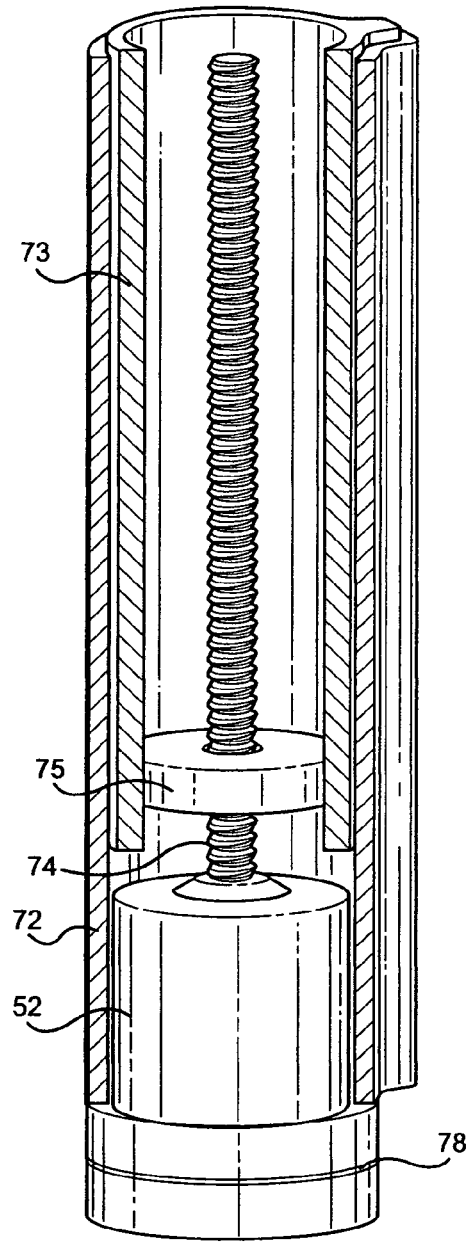
FIG. 6(c) is a side view of an internal screw drive system with rotary encoder and telescoping shaft as alternative to the external rack and pinion system in FIGS. 4 (c)-(f).

FIG. 6(*a*) through 6(*e*) show alternative drive systems for linear motion using rotating screws to drive linear motion, instead of the rack and pinion drives shown in FIG. 4(*a*) through 4(*g*). The illustrations show applications for raising and lowering clamp assemblies on vertical column 20 as well as extending and contracting fixtures on shafts 21.

In FIG. 6(*a*) is a perspective side view of column 20 with three fractional horsepower motors at the base capable of driving three parallel screws or bolts 68 that pass through three rings or collars 69a, 69b, and 69c that can support and be linked to the three clamp assemblies 22 shown in previous figures. In order for the collars to move independently, only one of the holes through each of the collars is threaded and in contact with the bolt the other holes having larger diameters, and therefore slideable along the bolts.

FIG. 6(*b*) is a view from the top of one of the collars showing the three holes 70a, 70b, and 70c. In our illustration, hole 70a would be threaded in collar 69a, with the other two holes unthreaded, 70b in collar 69b, and 70c in collar 69c with other holes unthreaded. The top of FIG. 6(*b*) shows a projection 71 which engages a slot running the length of vertical column 20 to prevent the collars from rotating as they are being driven by the bolts.

FIG. 6(*c*) is a side perspective view of a telescoping shaft with an internal drive system that could serve as an alternative to the rack and pinion systems shown in FIG. 4(*a*) through 4(*g*). The system consists of a motor 52 embedded in the base structure of the telescope 72 linked to the extendable section of the telescope 73 by means of a screw or bolt 74 that passes through and meshes with a threaded hole in a cylindrical member 75 rigidly affixed to extendable section 73.

FIG. 6(*d*) shows the telescoping extension of 73 from the base section 72 driven by the rotation of bolt 74. FIG. 6(*e*) is a top view showing an integral guide 76 rigidly attached to 73 encased in and sliding along slot 77 incorporated in the telescope base 72. This guide prevents 73 from rotating as it is extended through the rotary motion of bolt 74. The lower shaft of motor 52 is linked into a rotary encoder 78 which is capable of monitoring, and therefore controlling, the length of shaft extension, computed by the record number of turns of the motor detected by the rotary encoder.

FIGS. 7(*a*) and (*b*) show an alternate and preferred way of raising and lowering the clamp assemblies 22 on the vertical column 20, and extending and contracting shafts 21 by means of an integrated clamp assembly that contains motors linked to rack and pinion linear drives, with linear encoders detecting the range of motions, and rotary knobs that can manually lock down the assembly during the process of alignment. All settings can them be recorded digitally on a PDA or other electronic means.

Figure 7A:
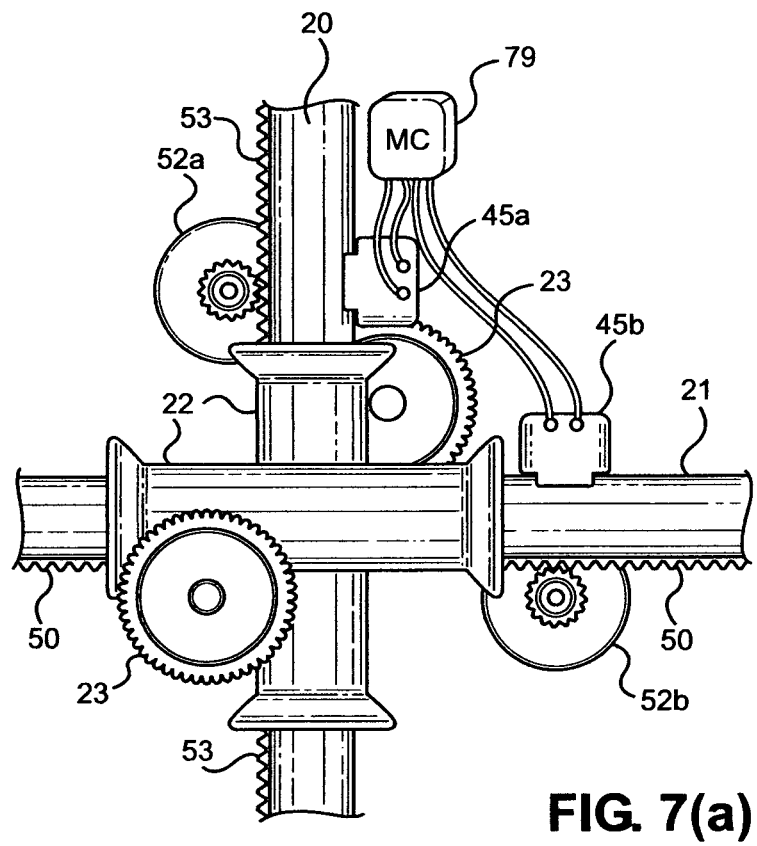
FIG. 7(a) is a side view of a clamp assembly with integrated linear transducers, drive motors, and tightening clamps on the vertical column and horizontal shafts.

FIG. 7(a) is a side view of the integrated clamp assembly 22 with motor 52a raising and lowering the clamp assembly 22 on the vertical column 20, via rack and pinion linear drive 53 and linear encoder 45a that records settings and provides data to the motor controller 79 (MC) for adjusting the height up and down with the reversible motor 52a. Likewise shaft 21 is able to be extended and contracted with motor 52b driving rack and pinion linear drive 50, with linear encoder 45a providing settings and data to the MC motor controller 79 to move fixtures back and forth on the horizontal shaft 21.

Figure 7B:
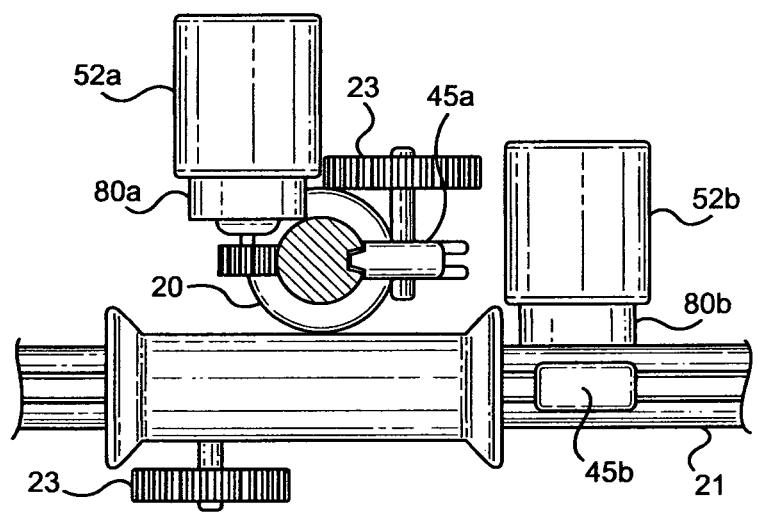
FIG. 7(b) is a top view of the integrated clamp assembly shown in FIG. 7(a).

FIG. 7(b) is a top view of the integrated clamp assembly 22 showing elements hidden in FIG. 7(a) including side views of motors 52a and 52b with reduction gearing 80a and 80b, and top views of linear transducer encoders 45 and rotating knobs 23 for locking down settings.

The specified placement of the components in FIGS. 7(a) and 7(b) is intended to be only one illustration of the potential integration of motors, drives, linear micro-encoders and rotatable knob clamps, around the clamp assembly 22, the junction of the vertical column 20 and the upper, mid, and lower horizontal shafts. It is not meant to be restrictive in any sense. One familiar with the art can see that these components can be placed at various locations around the nexus of the vertical column and horizontal shafts as long as they server the functions of vertical and horizontal motion, powered by motors 52, rack and pinion drives 50 or 53, with linear encoders 45 reading positional settings and controlling the motors via motor controllers 79, with adjacent rotary knobs 23 to lock down the settings.

Figure 8A:
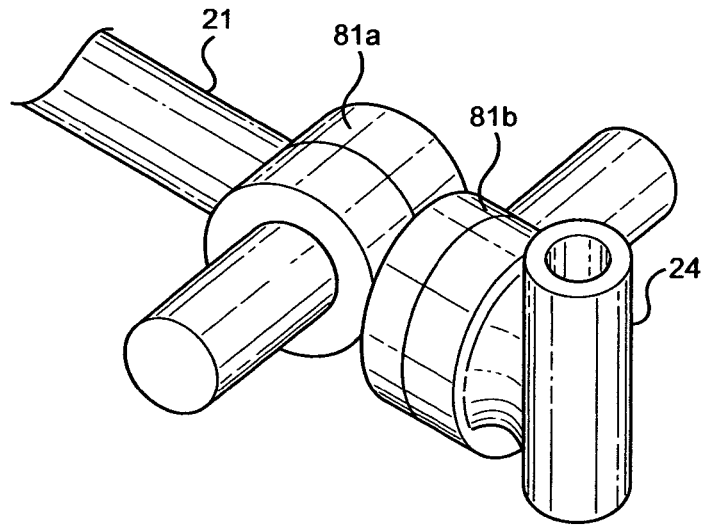
FIG. 8(a) is perspective view of upper level motorized socket clamp assembly in FIG. 3(b) showing two orthogonal motorized joints with integrated micro-micro-encoders.
Figure 8B:
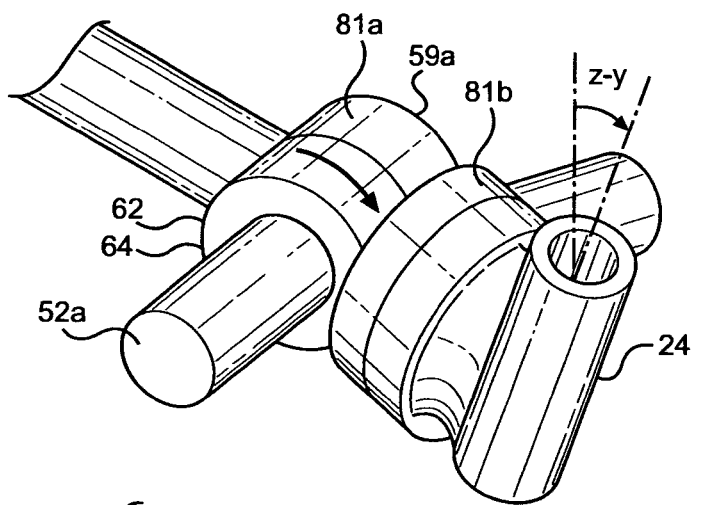
FIG. 8(b) is perspective view of clamp assembly in FIG. 8(a) with inner joint rotated clockwise in the Z-X plane.
Figure 8C:
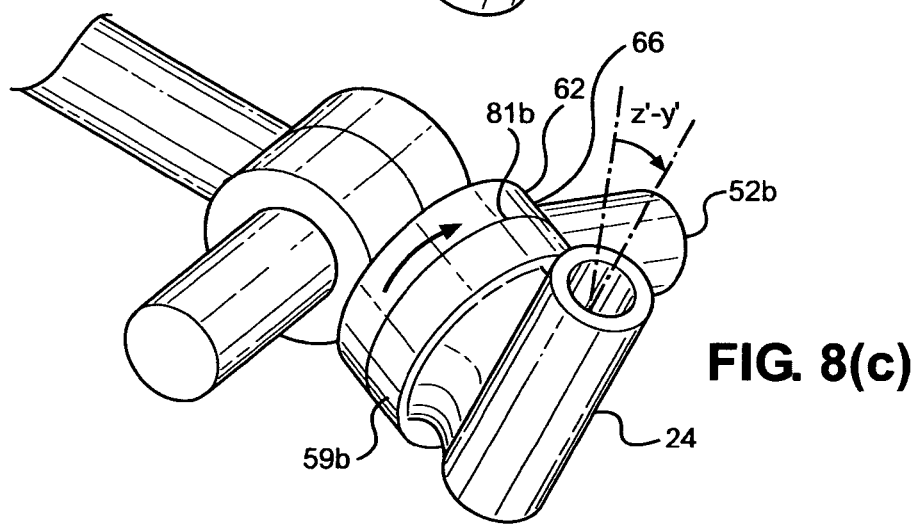
FIG. 8(c) is perspective view of clamp assembly in FIG. 8(a) with outer joint further rotated clockwise in the Z'-Y' plane, relative to a new coordinate system X', Y' and Z' gene.

FIG. 8(a) through 8(c) shows a motor-powered version of the fixture illustrated in FIG. 3(b). FIG. 8(a) shows shaft 21 with two rotary joints 81a and 81b that are capable of positioning the upper socket clamp assembly fixture 24 in three dimensions by sequential rotations of joints 81a and 81b.

Figure 5C:
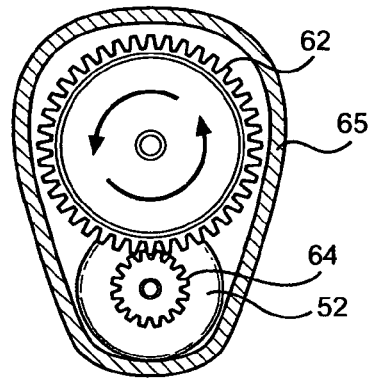
FIG. 5(c) is an end view of the reduction gear and motor that drives the rotation of one shaft relative to the other.

FIG. 8(b) shows a first rotation around 81a, where motor 52a, through planar gears 62 and 64 as illustrated in FIG. 5(c), rotates its connection to the outer assembly containing joint 81b in the (Z-Y) plane, with rotary micro-encoder 59a providing positioning information.

Figure 5D:
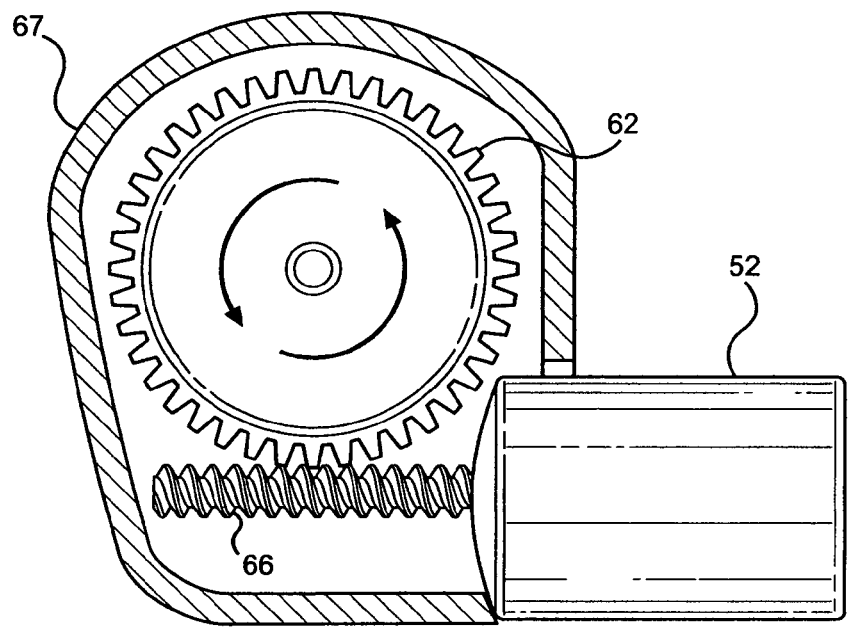
FIG. 5(d) is a view of an alternate drive system using a worm gear drive system attached to a motor perpendicular to the plane of the primary gear shown in FIG. 5 (c).
Figure 5E:
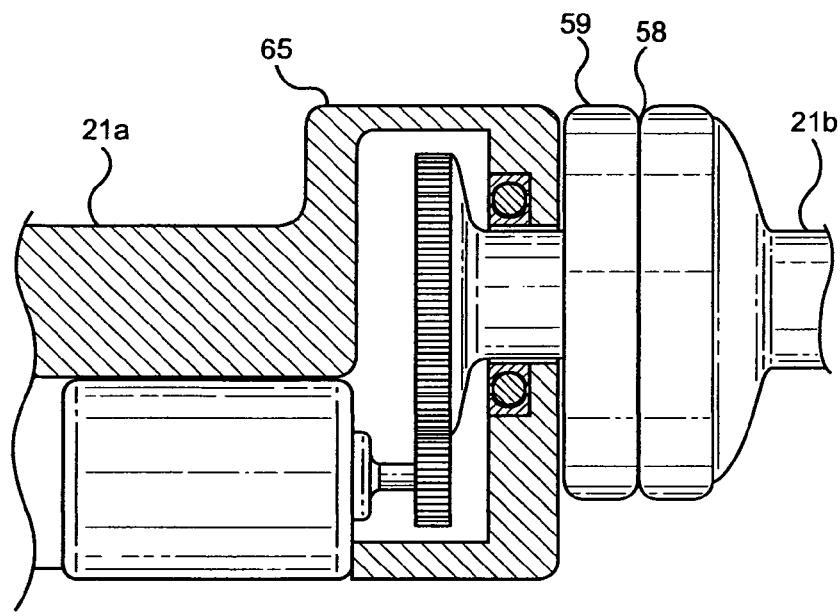
FIG. 5(e) is a side view of a rotary joint with a gear drive system shown in FIG. 5(c) coupled with the rotary micro-encoder shown in FIG. 5(a).

FIG. 8(c) shows a second rotation around 81b, where motor 52b, through planar gear 62 and worm gear 66 as illustrated in FIG. 5(d), rotates the outer assembly containing joint 81b in the (Z'-Y') plane, with rotary micro-encoder 59b providing positioning information. The (Z'-Y') plane is that which is defined by an altered coordinate system (X',Y',Z') created by the first rotation through the 81 a joint.

The placement of components in FIG. (8)a through 8(c), as with FIGS. 7(a) and 7(b), is intended to be only one illustration of the potential integration of motors, drives, rotary micro-encoders around the junctions of fixtures like 24, but applicable to other fixtures that hold component parts of the prosthesis as it is being integrated, like the mid, and lower horizontal shafts. It is not meant to be restrictive in any sense.

One familiar with the art can see that these components can be placed at various locations around two fixture joints as long as they server the functions of the 3-D orientation of fixtures through rotary joints, powered by motors 52, planer and worm-gear drives 62, 64, and 66, with rotary encoders 59 reading positional settings and controlling the motors. The same principles would hold relative to the rotation of only one joint, for example, the rotation of yoke 29 around the mid-level shaft 21.

In fixture 26, shown in FIG. 3(a) the platform ankle assembly with a moveable platform 34 can be positioned by a rotatable screw 39 motorized with a screw drive similar to those shown in FIG. 6, with either a linear or rotary encoder to determine lateral position.

Finally, although many of the fixtures, clamps and assemblies or similar to or relate to the popular Hosmer VFJ-100 Vertical Fabricating Jig, there are other specialized vertical and horizontal jigs, however, like the Berkeley Alignment Jig, BAJ-100, which perform similar functions. These can also be outfitted with motors, linear and rotational drives, linear and rotational encoders, clamping assemblies and rotational knobs and fixtures for locking down settings, that are similar to those described in this invention. The Digital Alignment Jig (DAJ) and the Automated Alignment Jig (AAJ) with fixtures specially designed for the positioning and alignment of prosthetic parts and components is a generalized concept applicable to a variety of forms and embodiments.

We claim:

1. An assembly jig for aligning and securing components during fabrication of prosthetic or orthotic devices, comprising:
 a mast having a longitudinal axis;
 three or more joint modules, each slideably coupled to the mast;
 three or more first linear encoding elements embedded into or on the mast, each first linear encoding element positioned to encode the location of one of the three or more joint modules;
 three or more orthogonal extensions, each orthogonal extension having:
  a proximal end slideably coupled through a one of the plurality of joint modules,
  a distal end terminating in a first end of a rotational joint,
  a fixture attached to a second end of the rotational joint,
  a second linear encoding element embedded into or on the orthogonal extension and configured to record the linear position of the rotational joint relative to its respective joint module,
  a rotational encoder located positioned to record a rotational position of the first rotational joint, and
  a fixture attached to the first rotational joint; and
 a plurality of electronic transmission devices such that each of the first linear encoding elements, each of the second linear encoding element, and each of the rotational encoding elements has a corresponding electronic transmission device that transmits positional data to a computerized centralized recording system,
 wherein a first orthogonal extension of the three or more orthogonal extensions has a first fixture configured to secure a pipe embedded into a plaster mold replica of a patient's truncated limb,
 wherein a second orthogonal extension of the three or more orthogonal extensions has a second fixture in the form of a clamp configured to secure prosthetic or orthotic components, and
 wherein a third orthogonal extension of the three or more orthogonal extensions has a third fixture in the form of a platform configured for securing prosthetic or orthotic components.

2. The assembly jig of claim 1, further comprising:
 three or more first motors attached to the mast, each being coupled to one of the three or more slideable joint modules, respectively;

three or more second motors, each mounted on one of the three or more joint modules and coupled via a second rack and pinion drive system to one of the three or more orthogonal extensions;

three or more third motors, each coupled to one of the rotational joint of the first orthogonal extension via a worm drive or a direct gear drive, configured to control roll, pitch and yaw of the rotational joint;

one or more fourth motors coupled to the second orthogonal extension via a telescoping shaft with an internal screw drive system; and one or more fifth motors with screw drives coupled to the platform of the third orthogonal extension configured to adjust the lateral movement of the platform, wherein each of the first, second, third, fourth, and fifth motors has a data transmission link to one of the first linear encoding elements, second linear encoding element, or rotational encoding elements allowing feedback loop control.

3. The assembly jig of claim 1, wherein the orthogonal extensions are fabricated from pipes or rods.

4. The assembly jig of claim 1, wherein the orthogonal extensions include extendable means for securing components.

5. The assembly jig of claim 1, wherein each of the joint modules is secured to the mast by means of either a knob or key, that compresses a portion of the joint module against the mast.

6. The assembly jig of claim 1, wherein each of the joint module are secured at the mast by means of a mechanical linkage between the joint module and one of the orthogonal extensions.

7. The assembly jig of claim 1, wherein each of the orthogonal extensions is secured to one of the joint modules by means of a knobs or key, that compresses a portion of the orthogonal extension against the joint module.

8. The assembly jig of claim 1, wherein each of the orthogonal extensions is secured to one of the joint modules by means of a mechanical linkage between the orthogonal extension and the joint module.

9. The assembly jig of claim 1, wherein the electronic transmission devices are either radio frequency transmitters or hardwire links.

10. The assembly jig of claim 1, wherein the first motors are coupled via a screw to the joint modules, and wherein the joint modules have machined corresponding to the pitch and diameter of the screw.

\* \* \* \* \*